(12) United States Patent
Weber et al.

(10) Patent No.: US 9,457,159 B2
(45) Date of Patent: Oct. 4, 2016

(54) SETTING OF PIERCING DEPTH

(75) Inventors: Wilfried Weber, Schopfloch (DE);
Andreas Renz, Sulz am Neckar (DE);
Dariusz Petry, Böblingen (DE)

(73) Assignee: Bayer Pharma Aktiengesellschaft, Berlin (DE)

(*) Notice: Subject to any disclaimer, the term of this patent is extended or adjusted under 35 U.S.C. 154(b) by 300 days.

(21) Appl. No.: 13/521,946

(22) PCT Filed: Dec. 23, 2010

(86) PCT No.: PCT/EP2010/007929
§ 371 (c)(1),
(2), (4) Date: Feb. 22, 2013

(87) PCT Pub. No.: WO2011/085797
PCT Pub. Date: Jul. 21, 2011

(65) Prior Publication Data
US 2013/0150787 A1 Jun. 13, 2013

(30) Foreign Application Priority Data
Jan. 13, 2010 (DE) .................... 20 2010 000 846 U

(51) Int. Cl.
*A61M 5/46* (2006.01)
*A61M 5/20* (2006.01)

(52) U.S. Cl.
CPC *A61M 5/46* (2013.01); *A61M 5/20* (2013.01)

(58) Field of Classification Search
CPC ............ A61M 5/2033; A61M 5/326; A61M 2005/206; A61M 5/46; A61M 5/24; A61M 5/28; A61M 2005/2403; A61M 2005/2433; A61M 2005/2437; A61M 2005/244
USPC ........................................... 604/117; 61/117
See application file for complete search history.

(56) References Cited

U.S. PATENT DOCUMENTS

| 2,322,245 A | 6/1943 | Lockhart |
| 4,790,823 A | 12/1988 | Charton et al. |

(Continued)

FOREIGN PATENT DOCUMENTS

| DE | 202009001836 | 5/2009 |
| EP | 0238378 | 9/1987 |

(Continued)

OTHER PUBLICATIONS

International Search Report for International Patent Application Publication PCT/EP2010/007929.

*Primary Examiner* — Nathan R Price
*Assistant Examiner* — Weng Lee
(74) *Attorney, Agent, or Firm* — Joseph L. Kent; David Schramm; James R. Stevenson

(57) ABSTRACT

An injection device including a carrier housing in which an injection unit having at least one injection liquid container that can be pressed out can be inserted, and an actuating device which can be driven along an injection direction (R) to activate the injection unit. The actuating device includes a piercing carriage a receptacle for the injection unit, and an injection carriage which can be displaced relative to the piercing carriage. The injection carriage has an actuating plunger for acting on a plunger of the injection unit. The piercing carriage and the injection carriage can be actuated by a force application means at least in order to carry out a piercing stroke and an injection stroke, and a piercing depth (tE) of the injection unit can be set. For this purpose, the receptacle is mounted on the piercing carriage adjustably in the injection direction (R).

19 Claims, 10 Drawing Sheets

(56) References Cited

U.S. PATENT DOCUMENTS

Figure 1:
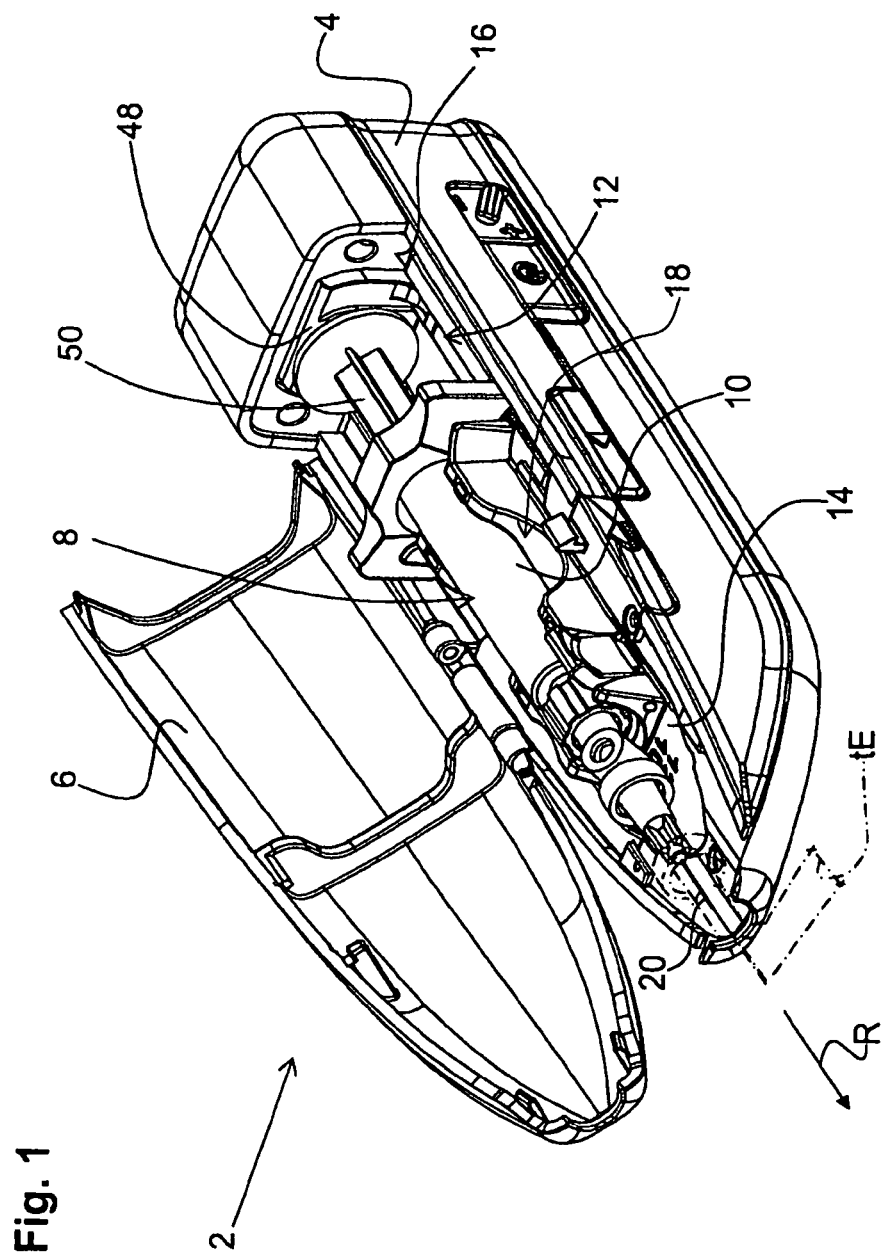

| | | |
|---|---|---|
| 7,297,136 B2 * | 11/2007 | Wyrick .................. 604/117 |
| 2001/0047151 A1 | 11/2001 | Xian |
| 2006/0258990 A1 * | 11/2006 | Weber .................. 604/208 |
| 2008/0015503 A1 * | 1/2008 | Jansen et al. .......... 604/117 |
| 2011/0202011 A1 * | 8/2011 | Wozencroft ............ 604/192 |
| 2011/0301534 A1 | 12/2011 | Renz et al. |

FOREIGN PATENT DOCUMENTS

| | | |
|---|---|---|
| JP | 6508773 | 10/1994 |
| JP | 2008522659 | 7/2008 |
| WO | 92/19296 | 11/1992 |
| WO | 2006/062788 | 6/2006 |

\* cited by examiner

SETTING OF PIERCING DEPTH

The invention relates to an injection device for medical applications, according to the preamble of claim 1. This injection device has a carrier housing into which an injection instrument, such as a syringe or a carpoule, with at least one injection-liquid container that can be squeezed out can be inserted. Moreover, the injection device has an actuation device, which can be driven along an injection direction in order to activate the injection instrument and comprises a piercing carriage, a receptacle for the injection instrument and an injection carriage which can be moved relative to the piercing carriage. Here, the injection carriage carries with it an actuation plunger, by means of which a plunger of an inserted injection instrument can be acted upon. In the process, the piercing carriage and the injection carriage can be actuated by a force-application apparatus, at least to carry out a piercing stroke, in which a piercing needle of the inserted injection instrument can be extended out of the carrier housing, and an injection stroke, in which a liquid can be pressed out of the injection-liquid container. Furthermore, means are provided on the injection device for setting a piercing depth; when said depth is reached the piercing stroke is complete and the injection stroke can be initiated.

DE 20 2009 001 836 U1 has disclosed an electromechanical injection device for medical applications. It has a piercing-depth stop which restricts the movement path of a piercing carriage and, as a result, determines a piercing depth. In doing so, the piercing-depth stop can be moved in a translational manner by an adjustment screw which is operable from outside of the carrier housing.

The advantage of such injection devices lies in the fact that the piercing depth can be set in a particularly simple manner and therefore also by the patient himself, for example. However, being able to set the piercing depth requires a relatively complicated mechanism because the piercing-depth stop, in its respective position, must be matched to the remaining means for controlling the piercing and injection stroke.

The object of the invention lies in providing an injection device which enables secure and simple setting of the piercing depth while having a simpler design.

This object is achieved by an injection device having the features of claim 1. Here, the receptacle for setting the desired piercing depth is adjustably mounted on the piercing carriage in the injection direction. This is how the piercing depth—the distance through which an injection needle of an injection instrument inserted into the injection device can be moved out of the carrier housing in the case of an intended application—is determined solely by the set position of the receptacle with respect to the injection carriage and by an unchanging end stop of the piercing carriage with respect to the carrier housing. The other means for controlling the piercing or injection stroke can, as a result of this, be designed to be at least largely independent of the set piercing depth, which in turn enables a simpler design of the injection device.

Provision is advantageously made for fixing means, by means of which the receptacle can be fixed with respect to the piercing carriage in a set or selected position. This makes it possible to permanently set the desired piercing depth.

Moreover, it is expedient if the fixing means have at least one engagement element, which can be made to engage with corresponding engagement counter-elements in one of several predetermined engagement positions, as a result of which particularly stable fixing of the receptacle with respect to the piercing carriage and hence the set piercing depth is ensured.

In a particularly advantageous embodiment of the injection device, the engagement can be established by a locking slide, which can be displaced between a locked position, in which locking means of the locking slide engage with locking counter-means of the piercing carriage, and a release position, in which the locking means and locking counter-means are not in engagement. As a result of this, detachable fixing of the receptacle on the piercing carriage is made possible by particularly simple means.

Here, it is expedient for the locking slide to be pretensioned in the locked position in order to fix the receptacle with respect to the piercing carriage until another piercing depth is set.

By contrast, in an embodiment of the injection device which is an alternative to this, the locking slide is pretensioned in the release position. This can prompt the respective user before each use to deliberately set a specific piercing depth which corresponds to the respectively provided application.

In the process, it is particularly advantageous if the locking slide can be moved by a handle, which, in the release position, projects into a receptacle space of the receptacle, i.e. the receptacle can be blocked by the handle. Hence, a set piercing depth can only be adjusted if no injection instrument is fixed in the receptacle. In the case of the embodiment with the locking slide pretensioned in the release position, the receptacle is moreover fixed to the piercing carriage and the piercing depth predetermined thereby is fixed when an injection instrument is inserted into the receptacle.

Moreover, it is expedient if the handle is formed by a first arm of a two-armed pivot member which is mounted such that it can pivot about a pivot axis and, on a second arm, has an eccentric cam for moving the locking slide, as a result of which comfortable actuation of the handle against the respective pretension is possible.

Moreover, provision is advantageously made on the piercing carriage for a display for determining the currently set piercing depth, which further simplifies setting one of several possible predetermined piercing depths.

In the process, it is expedient if the display has a scale extending in the injection direction, along which a pointer element of the receptacle can be displaced, as a result of which a current position of the receptacle with respect to the piercing carriage or the piercing depth predetermined thereby can be read off particularly well.

In an alternative particularly advantageous embodiment of the injection device, the receptacle and the piercing carriage can be moved with respect to one another via an adjustment mechanism, wherein the adjustment mechanism can be actuated by an adjustment wheel which is accessible from outside of the carrier housing. As a result of this, the position of the receptacle with respect to the piercing carriage and the piercing depth predetermined thereby can be set by the user in a particularly convenient manner.

In the process, it is expedient for the adjustment mechanism to have a spindle, which directly or indirectly meshes with the adjustment wheel via a toothed-wheel section and engages with a pick-up contour of the receptacle via a threaded section. Furthermore, the spindle is mounted in a rotatable manner on the piercing carriage. Such a spindle makes possible a particularly simple and cost-effective production of the adjustment mechanism.

In the process, it is particularly advantageous if the toothed-wheel section in a meshed position with the adjustment wheel can be moved on the latter by means of a gliding movement. In this manner, the adjustment wheel forms a type of sliding bearing in respect of the toothed-wheel section, allowing the meshing position of the two elements with respect to one another also to be maintained during a piercing stroke, which in turn simplifies the design of the injection device.

Moreover, it is advantageous if the engagement element is in this case formed by a housing-side latching lug, which can latch into one of several latching receptacles introduced into the adjustment wheel, as a result of which secure fixing of a set rotational position of the adjustment wheel or the corresponding translational position of the receptacle with respect to the piercing carriage and the correspondingly predetermined piercing depth can be ensured.

Figure 2:
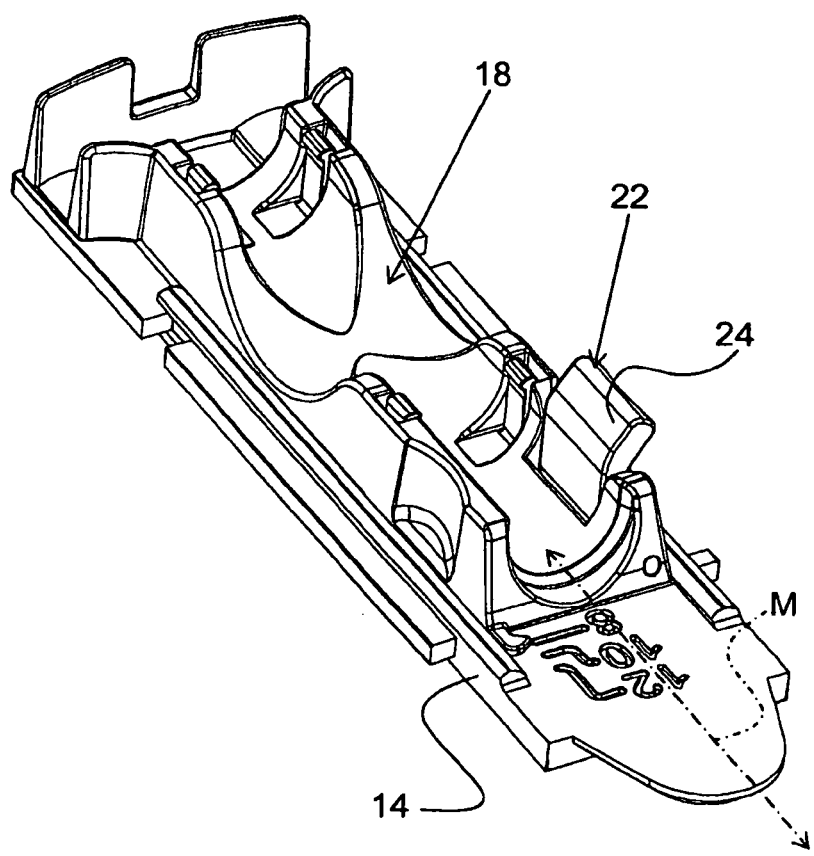
Figure 3A:
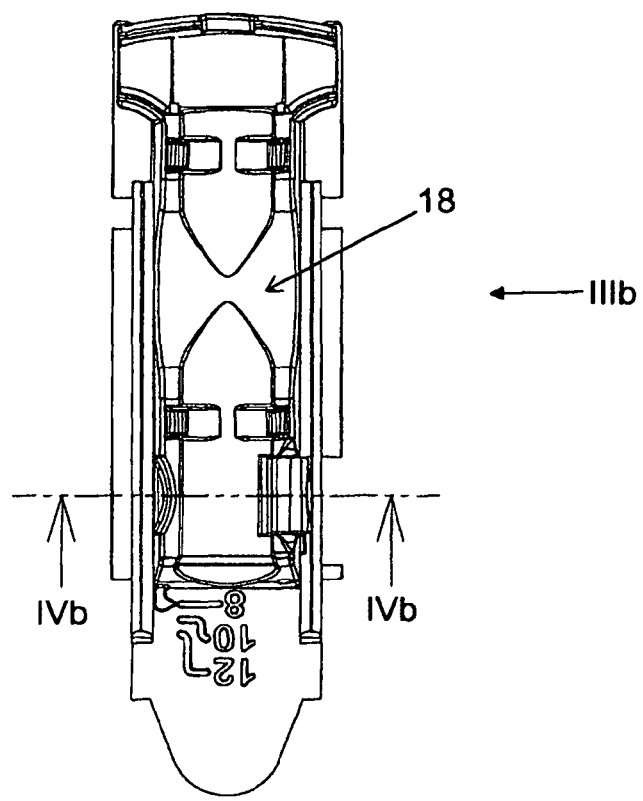
Figure 3B:
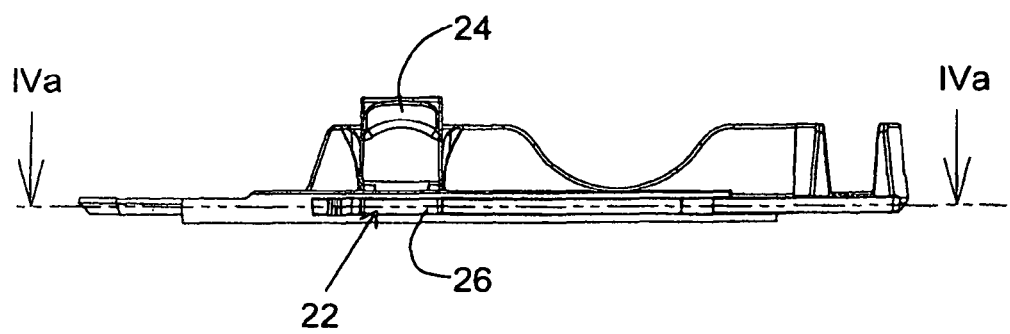
Figure 4A:
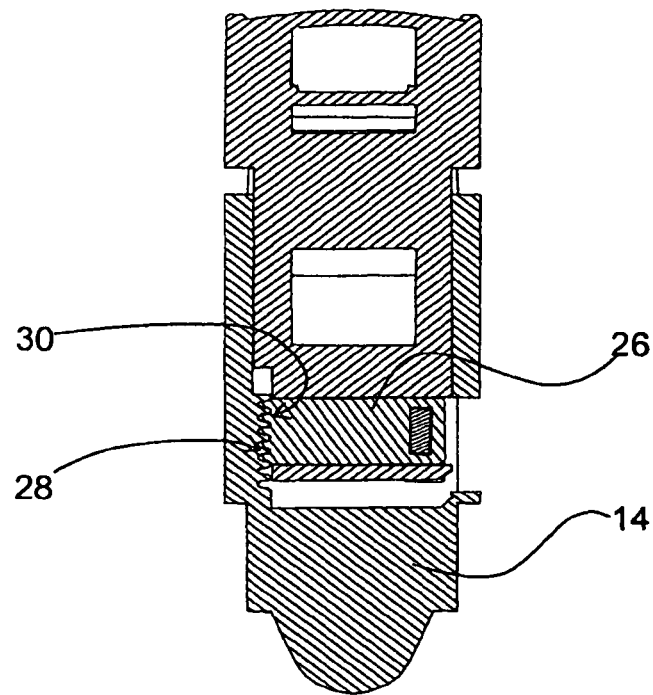
Figure 4B:
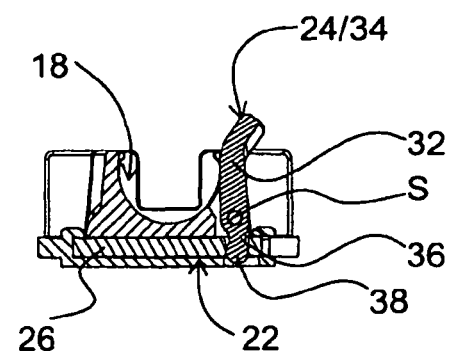
Figure 5:
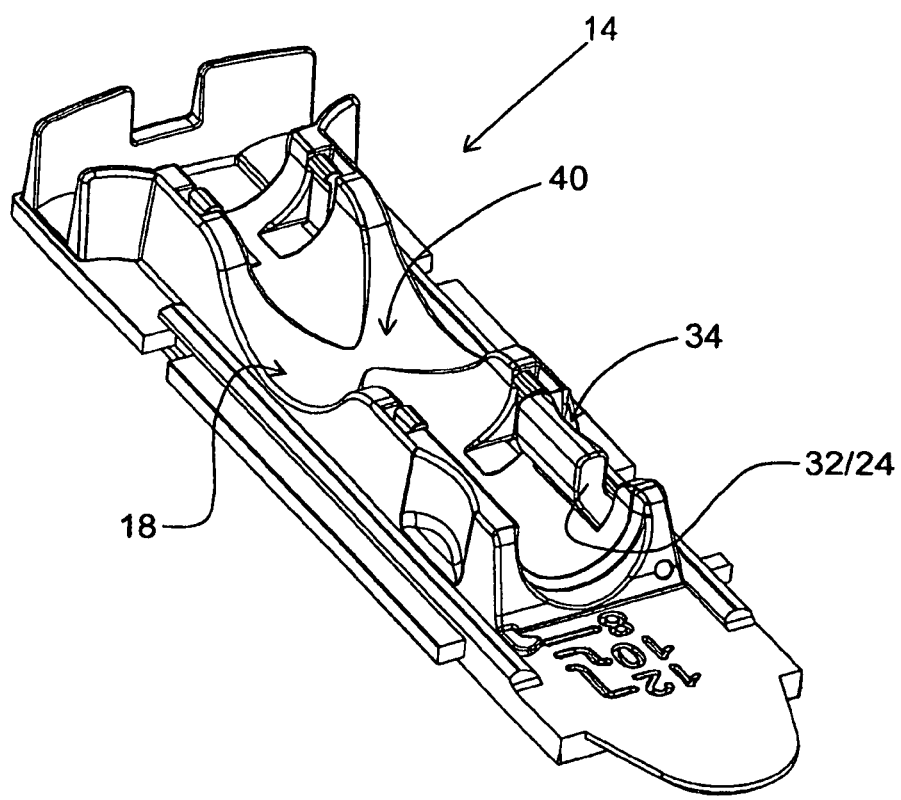
Figure 6A:
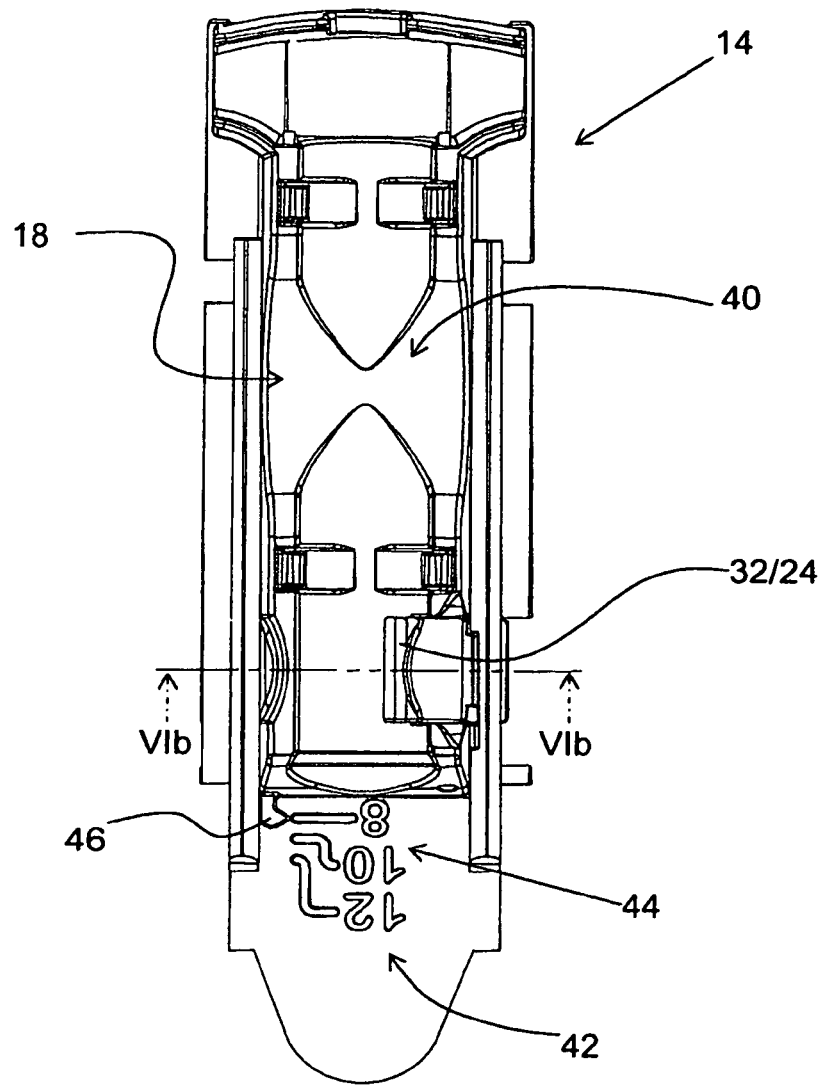
Figure 6B:
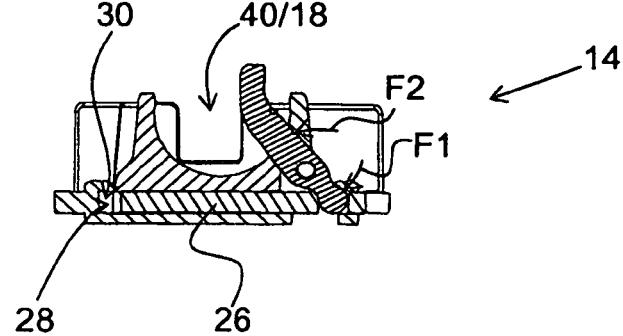
Figure 7:
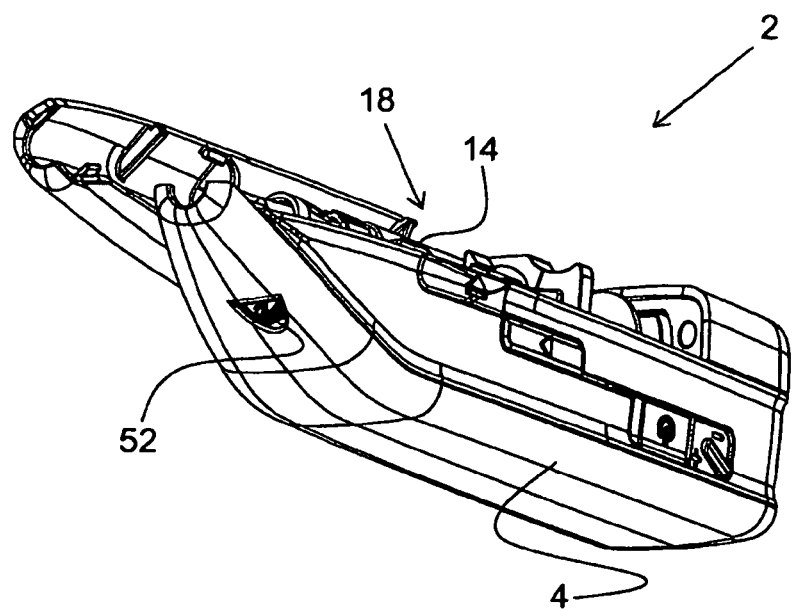
Figure 8:
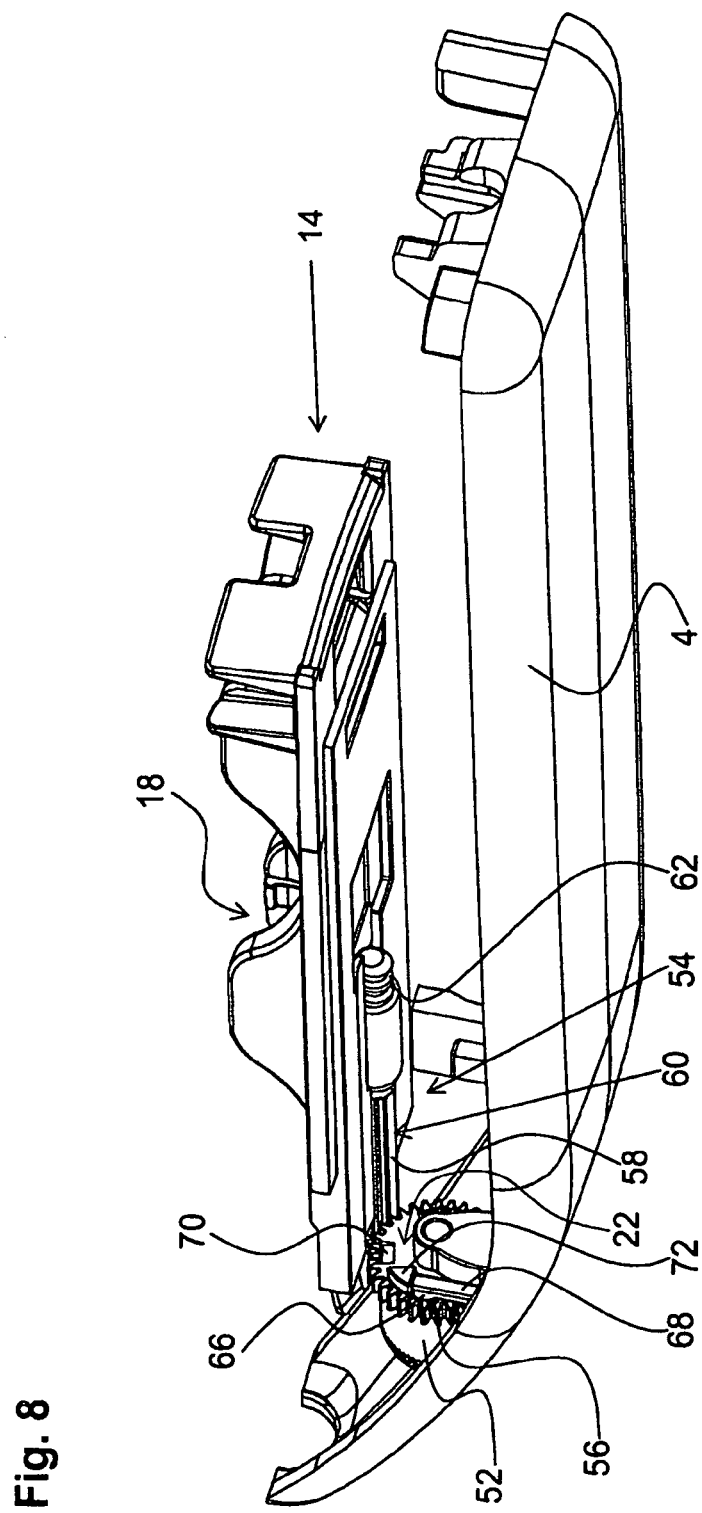
Figure 9A:
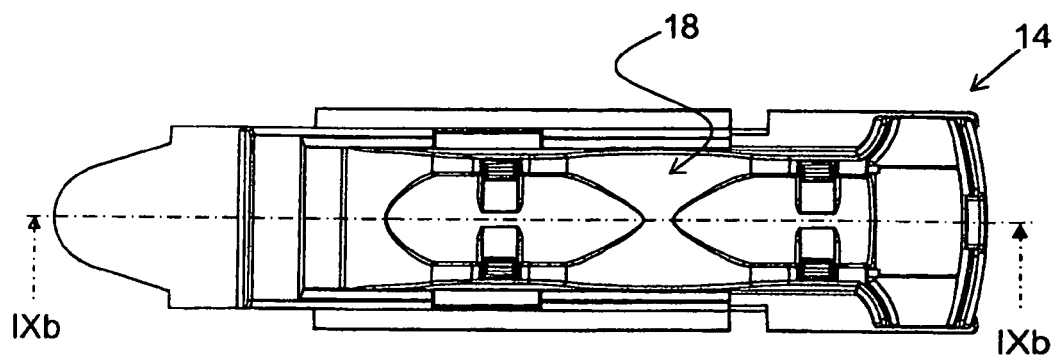
Figure 9B:
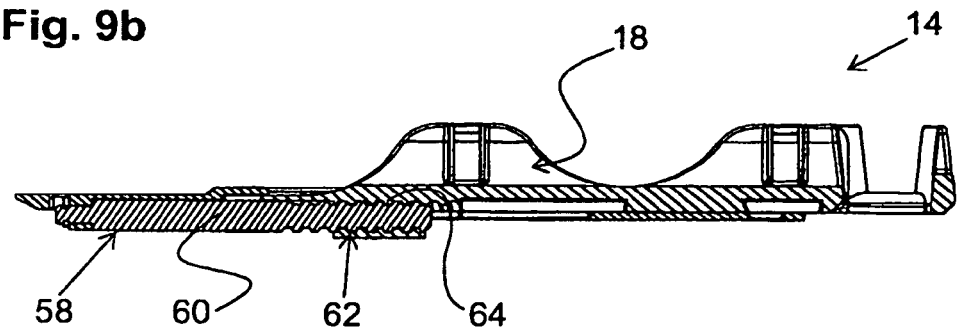
Figure 10:
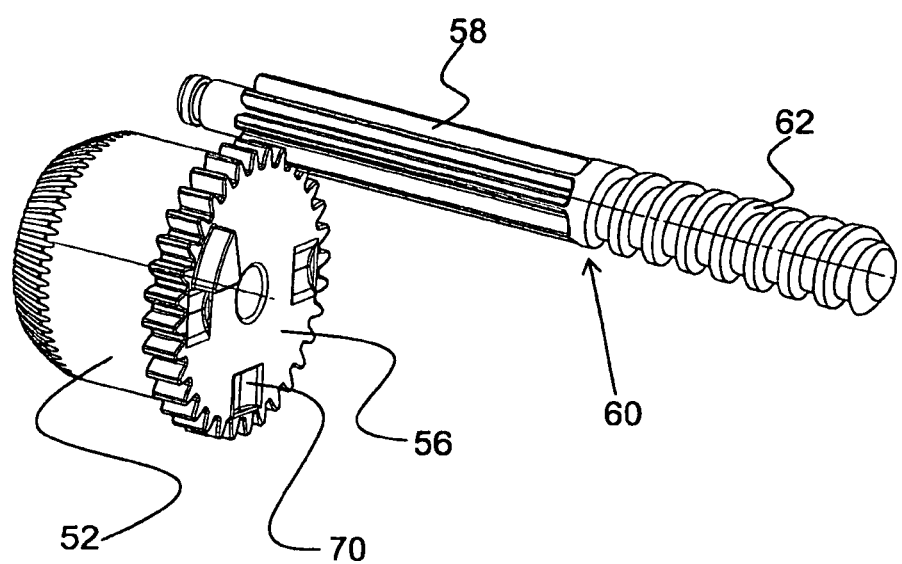

The figures illustrate an exemplary embodiment of the invention, in which:

FIG. 1 shows a perspective view of an injection device according to the invention with an inserted injection instrument, FIG. 2 shows a piercing carriage of the injection device according to FIG. 1, with an empty receptacle, FIG. 3a shows a plan view of the piercing carriage according to FIG. 2, FIG. 3b shows a lateral view of the piercing carriage in the direction IIIb from FIG. 3a, FIG. 4a shows a section in the plane IV.a from FIG. 3b, FIG. 4b shows a section in the plane IV.b from FIG. 3a, FIG. 5 shows a perspective illustration of the piercing carriage according to FIG. 2 in a release position, FIG. 6a shows a plan view of the piercing carriage according to FIG. 5, FIG. 6b shows a section in the plane VI.b from FIG. 6a, FIG. 7 shows a perspective view of an alternative embodiment of the injection device according to the invention with an inserted injection instrument, FIG. 8 shows a perspective cut-open view of an adjustment mechanism of the injection device according to FIG. 7, FIG. 9a shows a plan view of a piercing carriage of the injection device according to FIG. 7, with an empty receptacle, FIG. 9b shows a section in the plane IX.b from FIG. 9a, and FIG. 10 shows a perspective cut-out view of an adjustment wheel of the adjustment mechanism according to FIG. 8, meshing with a spindle.

FIG. 1 shows an injection device 2 according to the invention with a carrier housing 4, when the cover 6 is opened. A syringe-shaped injection instrument 8 with an injection-liquid container 10 has been inserted into the injection device 2. Here, for the purpose of holding and moving the injection instrument 8 along an injection direction R, the injection device 2 has an actuation device 12, which has a piercing carriage 14 with a receptacle 18 into which the injection instrument 8 can be inserted and an injection carriage 16 by means of which the injection instrument 8 can be squeezed out and which can be moved with respect to the piercing carriage 14.

In order to be able to set a predetermined piercing depth tE—through which, as illustrated by dash-dotted lines, an injection needle 20 of the injection instrument 8 can be moved out of the carrier housing 4—for an intended application, the receptacle 18 is mounted in a displaceable manner parallel to the injection direction R with respect to the remaining piercing carriage 14, as illustrated by arrow M in FIG. 2.

Provided on the receptacle 18 there are fixing means 22, by means of which said receptacle can be fixed on the piercing carriage in one of several positions; this can be gathered from FIGS. 3a, 3b, 4a and 4b. Here, the fixing means 22 have an engagement element in the form of a locking slide 26, which can be adjusted by a handle 24 and has locking means 28 in the form of teeth at one end facing away from the handle 24. These locking means 28 can be brought into engagement with locking counter-means 30, the latter being embodied in a complementary manner to the locking means 28; this can be gathered from FIG. 4a in particular. This is how the locking counter-means 30, which are embodied as toothed section, form an engagement counter-element, on which the locking slide 26 can be made to engage into one of several possible engagement positions. This is how the piercing carriage 14 and the receptacle 18 assume a locking position with respect to one another, in which the receptacle 18 is fixed to the remaining piercing carriage 14.

As can be gathered from FIG. 4b in particular, the handle 24 is formed by a first arm 32 of a two-armed pivot member 34, which is held on the receptacle 18 such that it can pivot about a pivot axis S. A second arm 36 of the pivot member 34 forms an eccentric cam 38 which engages with the locking slide 26.

As a result of pivoting the first arm 32 around the pivot axis S into a receptacle space 40 partly delimited by the receptacle 18, the piercing carriage 14 can be brought into a release position, as illustrated in FIGS. 5, 6a and 6b. During this pivoting of the pivot member 34, the locking means 28 of the locking slide 26 are made to disengage from the locking counter-means 30 (see FIG. 6b), and so the receptacle 18 can be displaced in the injection direction R with respect to the remaining piercing carriage 14 in order to set a new piercing depth tE.

In order, in the process, to be able to set a precise value for the piercing depth tE, a display 42 is provided on the piercing carriage 14, as can be gathered from FIG. 6a in particular; said display has a scale 44 of a plurality of settable values, along which a pointer element 46 fixedly connected to the receptacle 18 can be displaced.

As soon as the receptacle 18 is displaced with respect to the remaining piercing carriage 14 such that the pointer element 46 points at a desired value of the scale 44, the handle 24 is once again pivoted out of the receptacle space 40 and, as a result of this, the locking means 28 of the locking slide 26 is brought into engagement with the locking counter-means 30 in the corresponding engagement position and it follows that the locking position between the piercing carriage 14 and the receptacle 18 is reestablished. By inserting the injection instrument 8 into the receptacle 18, it is then possible to block the handle 24 to the extent that it can no longer be pivoted into the receptacle space 40. Hence, this also fixes the locking slide 26 in the engagement position with the locking counter-means 30. Thus, in order to be able to readjust the value of the set injection depth tE, it would initially be necessary to once again remove the injection instrument 8 from the receptacle 18.

Furthermore, an elastic force which pretensions the pivot member 34 in an end position may be provided on the latter, as indicated in FIG. 6b by arrows F1 and F2.

In the embodiment with the elastic force F1, the pivot member 34 is in the process pretensioned in the locking position as per FIGS. 2 to 4b, and so a set piercing depth tE remains permanently fixed until a new piercing depth tE is set by actuating the handle 24 and displacing the receptacle 18 with respect to the remaining piercing carriage 14.

As an alternative to this, the pivot member 34 is pretensioned in the release position as per FIGS. 5 to 6b in the embodiment with the elastic force F2. As a result of this, a user is prompted to deliberately set a specific piercing depth tE when an injection instrument 8 is inserted into the receptacle 18.

After the piercing depth tE has been set and after the injection instrument 8 has been inserted, the injection device 2 can then be triggered when the cover 6 is closed. In the process, the actuation device 12 is acted upon by an e.g. purely mechanical or electromechanical force application apparatus (not illustrated in any more detail) of the actuation device such that, during a piercing stroke, the piercing carriage 14 and the injection carriage 16 are together moved in the injection direction R until the piercing needle 20 projects out of the carrier housing 4 over the piercing depth tE. Subsequently, it is then only the injection carriage 16 which is moved on in the injection direction R, wherein an actuation plunger 48 of the injection carriage 16 (as per FIG. 1) presses against a plunger 50 of the injection instrument 8, by means of which plunger the injection-liquid container 10 is squeezed out.

FIGS. 7 to 10 show an alternative embodiment of the injection device 2, in which the receptacle 18 can, for the purposes of setting the desired piercing depth tE, be adjusted with respect to the remaining piercing carriage 14 by means of an adjustment wheel 52 which can be actuated from outside of the carrier housing 4. Otherwise the injection device 2 corresponds to the embodiment described in respect of FIGS. 1 to 6b.

To this end, provision is made between the adjustment wheel 52 and the receptacle 18 for an adjustment mechanism 54, as can be gathered from FIG. 8. Said adjustment mechanism has a toothed wheel 56, which is connected to the adjustment wheel 52 and meshes with a toothed-wheel section 58 of a spindle 60. This spindle 60 is rotatably mounted on an underside of the piercing carriage 14. The spindle 60 moreover has a threaded section 62, which engages with a pick-up element 64 of the receptacle 18, as can be gathered from FIG. 9b.

Thus, as a result of rotating the adjustment wheel 52, the spindle 60 is rotated by means of the toothed wheel 56, as a result of which in turn the pick-up element 64 is moved along the injection direction R by the co-rotating threaded section 62 of the spindle 60.

In order, in the process, to be able to set a precise value of the piercing depth tE, a number of possible values are introduced into the adjustment wheel 52, of which the respectively set value can be read off from outside of the carrier housing 4 (see FIG. 7). Here, each settable value corresponds to a specific position of the adjustment wheel 52, or the adjustment mechanism 54 overall, which can be fixed by the fixing means 22, as illustrated in FIG. 8.

To this end, the fixing means 22 in this embodiment of the injection device 2 have a latching lug 66 acting as engagement element, which is held on the carrier housing 4 by a spring arm 68 (see FIG. 8). Said latching lug can latch with respectively one of several latching receptacles 70 connected to the adjustment wheel 52 or toothed wheel 56. Here each position of the adjustment mechanism 54, which can be fixed in this way by means of the latching lug 66 and one of the latching receptacles 70, corresponds to one of the displayable values of the piercing depth tE.

As an alternative to the illustrated fixing means 22, it is also possible to set the toothings of the adjustment mechanism 54 by an appropriate selection of the tooth angles or tolerances such that the adjustment mechanism 54 remains in a set rotational position as a result of a self-locking feature alone.

Furthermore, provision is made on the toothed wheel 56 for a rotational stop 72, which, as illustrated, butts against the spring arm 68 in an end position, as a result of which overwinding of the adjustment wheel 52 is avoided.

After setting the piercing depth tE desired for the intended application, the injection device 2 can thereupon be operated in accordance with the procedure described for the first embodiment.

The invention claimed is:

1. An injection device comprising:
    (a) a carrier housing into which an injection instrument with at least one injection-liquid container that can be squeezed out can be inserted, and
    (b) an actuation device which can be driven along an injection direction in order to activate the injection instrument, said actuation device comprising a piercing carriage, a receptacle for the injection instrument, and an injection carriage which can be moved relative to the piercing carriage and has an actuation plunger for acting on a plunger of the injection instrument,
    wherein the piercing carriage and the injection carriage can be actuated by a force-application apparatus, at least to carry out a piercing stroke and an injection stroke, and a piercing depth of the injection instrument can be set, and
    wherein the receptacle is adjustably mounted on the piercing carriage in the injection direction.

2. The injection device as claimed in claim 1, wherein fixing means are provided, by means of which the receptacle can be fixed with respect to the piercing carriage in a set position.

3. The injection device as claimed in claim 2, wherein the fixing means have at least one engagement element which can be made to engage with corresponding engagement counter-elements in one of several predetermined engagement positions.

4. The injection device as claimed in claim 3, wherein the engagement can be established by a locking slide which can be displaced between a locked position, in which locking means of the locking slide engage with locking counter-means of the piercing carriage, and a release position, in which the locking means and locking counter-means are not in engagement.

5. The injection device as claimed in claim 4, wherein the locking slide is pretensioned in the locked position.

6. The injection device as claimed in claim 4, wherein the locking slide is pretensioned in the release position.

7. The injection device as claimed in claim 5, wherein the locking slide can be moved by a handle which, in the release position, projects into a receptacle space of the receptacle.

8. The injection device as claimed in claim 7, wherein the handle is formed by a first arm of a two-armed pivot member, wherein the two-armed pivot member is mounted such that it can pivot about a pivot axis and wherein the handle has an eccentric cam for moving the locking slide on a second arm.

9. The injection device as claimed in claim 1, wherein a display for determining the currently set piercing depth is provided on the piercing carriage.

10. The injection device as claimed in claim 9, wherein the display has a scale extending in the injection direction, along which a pointer element of the receptacle can be displaced.

11. The injection device as claimed in claim 3, wherein the receptacle and the piercing carriage can be moved with respect to one another via an adjustment mechanism which is actuatable by an adjustment wheel.

12. The injection device as claimed in claim 11, wherein the adjustment mechanism has a spindle which meshes with the adjustment wheel via a toothed-wheel section, engages with a pick-up contour of the receptacle via a threaded section, and is mounted in a rotatable manner on the piercing carriage.

13. The injection device as claimed in claim 12, wherein the toothed-wheel section in a meshed position with the adjustment wheel can be moved on the latter by means of a gliding movement.

14. The injection device as claimed in claim 6, wherein the locking slide can be moved by a handle which, in the release position, projects into a receptacle space of the receptacle.

15. The injection device as claimed in claim 2, wherein the receptacle and the piercing carriage can be moved with respect to one another via an adjustment mechanism which is actuatable by an adjustment wheel.

16. The injection device as claimed in claim 3, wherein the receptacle and the piercing carriage can be moved with respect to one another via an adjustment mechanism which is actuatable by an adjustment wheel.

17. The injection device as claimed in claim 12, wherein the at least one engagement element is formed by a housing-side latching lug which can latch into one of several latching receptacles introduced into the adjustment wheel.

18. The injection device as claimed in claim 13, wherein the at least one engagement element is formed by a housing-side latching lug which can latch into one of several latching receptacles introduced into the adjustment wheel.

19. The injection device as claimed in claim 16, wherein the at least one engagement element is formed by a housing-side latching lug which can latch into one of several latching receptacles introduced into the adjustment wheel.

* * * * *